United States Patent
Janaway et al.

(10) Patent No.: US 10,453,557 B2
(45) Date of Patent: Oct. 22, 2019

(54) METHODS AND SYSTEMS FOR VISUALIZING AND EVALUATING DATA

(71) Applicant: LIFE TECHNOLOGIES CORPORATION, Carlsbad, CA (US)

(72) Inventors: Gordon A. Janaway, Castro Valley, CA (US); Manjula Aliminati, Foster City, CA (US); Ruoyun Wu, Singapore (SG); David Fortescue, San Francisco, CA (US); Ming Shen, Singapore (SG)

(73) Assignee: Life Technologies Corporation, Carlsbad, CA (US)

( * ) Notice: Subject to any disclaimer, the term of this patent is extended or adjusted under 35 U.S.C. 154(b) by 5 days.

(21) Appl. No.: 14/347,864

(22) PCT Filed: Sep. 28, 2012

(86) PCT No.: PCT/US2012/057716
§ 371 (c)(1),
(2) Date: Mar. 27, 2014

(87) PCT Pub. No.: WO2013/049443
PCT Pub. Date: Apr. 4, 2013

(65) Prior Publication Data
US 2014/0236496 A1 Aug. 21, 2014

Related U.S. Application Data

(60) Provisional application No. 61/660,960, filed on Jun. 18, 2012, provisional application No. 61/541,342, filed on Sep. 30, 2011.

(51) Int. Cl.
*G16B 40/00* (2019.01)
*C12Q 1/6851* (2018.01)

(52) U.S. Cl.
CPC ............ *G16B 40/00* (2019.02); *C12Q 1/6851* (2013.01)

(58) Field of Classification Search
None
See application file for complete search history.

(56) References Cited

U.S. PATENT DOCUMENTS

| 2006/0223169 A1 | 10/2006 | Bedingham et al. |
| 2009/0239308 A1 | 9/2009 | Dube et al. |
| 2010/0173394 A1 | 7/2010 | Colston et al. |

FOREIGN PATENT DOCUMENTS

| JP | 5591707 B2 | 9/2014 |
| WO | 2011/100604 | 8/2011 |

OTHER PUBLICATIONS

Bhat et al (Analytical and Bioanalytical Chemistry, Springer, Berlin, DE vol. 394 No. 2 Mar. 15, 2009, pp. 457-467).*
Vogelstein et al. PANS vol. 96 No. 16 Aug. 3, 1999, pp. 9236-9241.*
Larson et al. (WO2011/100604).*
Colston et al. (US2010/173394).*
Dube et al (US2009/239308).*
Bhat, Somanath et al., "Single Molecule Detection in Nanofluidic Digital Array Enables Accurate Measurement of DNA Copy Number", *Anal Bioanal Chem*, vol. 394, 2009, 457-467.
Vogelstein, et al., "Digital PCR", *Proc. Natl. Acad. Sci. USA.*, vol. 96, Aug. 1999, 9236-9241.
Weaver, et al., Taking qPCR to a higher level: Analysis of CNV reveals the power of high throughput qPCR to enhance quantitative resolution, Methods, Jan. 2010, pp. 271-276, vol. 50, Elsevier Inc.
International Search Report and Written Opinion, International Application No. PCT/US2012/057716, dated Dec. 20, 2012, 8 pages.

* cited by examiner

*Primary Examiner* — Joseph Woitach
(74) *Attorney, Agent, or Firm* — Mauriel Kapouytian Woods LLP; Lana Akopyan; Michael Mauriel

(57) ABSTRACT

A computer-implemented method of generating a digital polymerase chain reaction (dPCR) result is provided. The method includes detecting a first set of emission data from a plurality of samples, each included in a sample region of a plurality of sample regions, at a first time during an amplification period. The method further includes determining a positive or negative amplification determination for each sample of the plurality of samples based in part on the first set of emission data. A dPCR result is generated based on the positive or negative amplification determinations for the plurality of samples.

31 Claims, 11 Drawing Sheets

METHODS AND SYSTEMS FOR VISUALIZING AND EVALUATING DATA

CROSS-REFERENCE TO RELATED APPLICATIONS

This application claims the benefit of priority of U.S. provisional application Ser. No. 61/541,342, filed Sep. 30, 2011, and U.S. provisional application Ser. No. 61/660,960, filed Jun. 18, 2012, both of which are incorporated herein by reference in their entireties.

BACKGROUND

Polymerase Chain Reaction (PCR) instrumentation has made it possible to perform reliable quantification of DNA or RNA levels in biological samples. Commercially available PCR instruments, and related data acquisition and analysis software, process qPCR assay data generated from biological samples. These systems report quantitative results by calculating a quantification cycle ($C_q$, $C_T$ or $C_{RT}$) value as the fractional PCR cycle number where the reporter signal rises above a threshold set manually by a human or automatically by software. The determined $C_q$ value can be used to estimate the initial quantity of DNA material.

In contrast to qPCR, a Digital PCR (dPCR) result set often requires analysis of several thousand PCR reactions. Generally, increasing the number of replicates increases the accuracy and reproducibility of dPCR results.

Digital Polymerase Chain Reaction (dPCR) is a method that has been described, for example, in U.S. Pat. No. 6,143,496 to Brown et al. Results from dPCR can be used to detect and quantify the concentration of rare alleles, to provide absolute quantitation of nucleic acid samples, and to measure low fold-changes in nucleic acid concentration.

One example of implementation of dPCR is often performed using apparatus adapted from conventional qPCR, in which replicates are arrayed in a two dimensional array format including m rows by n columns, i.e., an m×n format. PCR cycling and read-out (end-point or real-time) generally occurs within the same array. A maximum of m×n replicates can be processed in a single batch run.

The (m×n) format in most quantitative polymerase chain reaction (qPCR) platforms is designed for sample-by-assay experiments, in which PCR results need to be addressable for post-run analysis. For dPCR, however, the specific position or well of each PCR result may be immaterial and only the number of positive and negative replicates per sample may be analyzed.

The read-out of dPCR, that is, the number of positive reactions and the number of negative reactions, is linearly proportional to the template concentration, while the read-out of qPCR (signal vs. cycle) is proportional to the log of the template concentration. For this reason, dPCR typically is constrained to a narrow dynamic range of template input. As a result of the log versus linear, the dPCR analysis offers better resolution for close fold changes than qPCR. Furthermore, the resolution remains approximately linear across the entire dynamic range that is supported.

However, to determine positive and negative counts for a dPCR result after thermal cycling, also known as endpoint reads, requires determining or setting a fluorescence threshold. Thus, it is a challenge to determine where a threshold should be set to accurately distinguish between negatives and positives because there may be no or low amplifications for each sample. Furthermore, it is also a challenge to determine whether a sample volume contains one copy or multiple copies, for example.

SUMMARY

In one exemplary embodiment, a computer-implemented method of generating a digital polymerase chain reaction (dPCR) result is provided. The method includes detecting a first set of emission data from a plurality of samples, each included in a sample region of a plurality of sample regions, at a first time during an amplification period. The method further includes determining a positive or negative amplification determination for each sample of the plurality of samples based in part on the first set of emission data. A dPCR result is generated based on the positive or negative amplification determinations for the plurality of samples.

DETAILED DESCRIPTION

Figure 1:
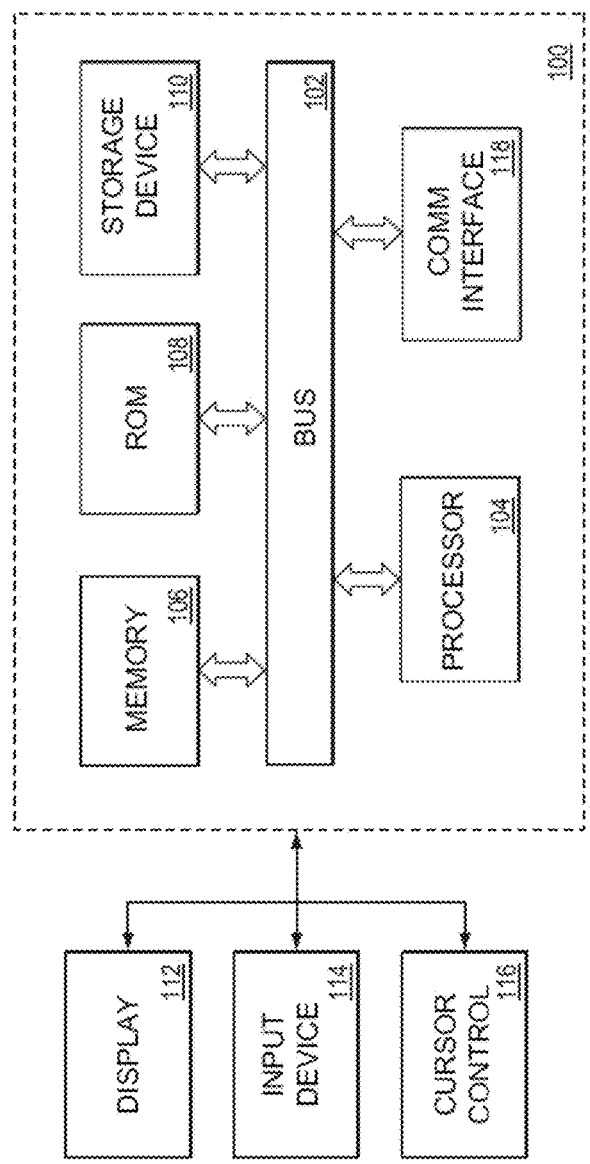
FIG. 1 is a block diagram that illustrates a computer system, upon which embodiments of the present teachings may be implemented.

Exemplary systems for methods related to the various embodiments described in this document include those described in U.S. Provisional Patent Application No. 61/541,453, U.S. Provisional Patent Application No. 61/541,342, U.S. Provisional Patent Application No. 29/403,049, U.S. Provisional Patent Application No. 61/541,495, U.S. Provisional Patent Application No. 61/541,366, and U.S. Provisional Patent Application No. 61/541,371, all of which are filed Sep. 30, 2011, and all of which are also incorporated herein in their entirety by reference.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

The present application relates to visualizing a large amount of data and, more particularly to, visualizing, clustering, and analyzing polymerase chain reaction (PCR) results.

According to various embodiments described herein, real-time amplification curves may be used in conjunction with a digital PCR (dPCR) analysis to verify that true amplification occurred. In some embodiments, amplification can be confirmed by determining if corresponding quantitative $C_q$ results are accurate. By being able to compare a positive/negative determination for a sample to its corresponding real-time amplification data, dPCR results may be determined with more accurate and higher confidence. Further, comparing real-time amplification data with the dPCR positive/negative determination presents a method of confirming and validating data.

However, as discussed above, for dPCR results, a large number of samples are analyzed. Thus, when real-time data is collected for every PCR reaction, such data displayed in a single plot to a user makes it very difficult to visually distinguish a true amplification, from low amplification or no amplification.

According to various embodiments, systems, methods, and computer-executable instructions for presenting a user interface to a user that allows selection of a sample of interest and allows the user to visually compare the positive/negative dPCR determination and its corresponding real-time amplification curve data may allow for higher confidence in a dPCR result. In some embodiments, a user may select one sample out of a plurality of samples and be provided a display of the selected sample's amplification data and corresponding dPCR positive/negative determination. In this way, a user may also be able to identify a certain group of samples that had low or no amplification to troubleshoot an experiment. For example, the user may be able to determine a portion of the sample regions that suffered from abnormal amplification due to excessive noise, contamination, or cross-talk. Further, using this information, a user may be able to locate a particular portion of the substrate containing the plurality of sample regions where contamination occurred, for example.

Further, to facilitate visualization and analysis, according to various embodiments described herein, histograms of $C_q$ values are displayed to a user aligned with the real time amplification curves to distinguish amplifications from non-amplifications. Sample regions with one or more copies of the sample should segregate into their respective peaks in histogram and will be distinct from non-amplification peaks (peaks at maximum cycles, no $C_q$). This visualization, according to various embodiments, enables detection of $C_T$ ranges for amplification, low amplifications, and non-amplifications.

In other embodiments, Rn values may also be determined and binned so that a histogram may also be generated. In this way, wells that have one copy, two copies, etc may be determined.

In various embodiments, the devices, instruments, systems, and methods described herein may be used to detect one or more types of biological components of interest. These biological components of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convection, infrared mediated thermal cycling, or helicase dependent amplification, for example. In some embodiments, the chip may be integrated with a built-in heating element.

According to various embodiments, detection of a target may be, but is not limited to, fluorescence detection, detection of positive or negative ions, pH detection, voltage detection, or current detection, alone or in combination, for example.

The methods and systems according to various embodiments described herein may be used in an application area where there are multiple discreet variables associated with a single entity for data analysis. According to various embodiments, some variable values may not all be entered manually by a system user. Although the following description pertains to user-defined sample support device setup using PCR systems, one skilled in the art can appreciate that the systems and methods described here can be applied to similar systems that employ high density sample support devices. A non-limiting example of such similar systems includes protein analysis systems, oligonucleotide array systems, sequencing systems, or any other system or instrument that performs experiments on a plurality of samples.

In quantitative PCR (qPCR), researchers and scientists visualize real-time amplification curves of samples to verify that true amplification occurred. A true amplification may indicate the quantitative $C_q$ results that were obtained are accurate. In contrast to qPCR, a digital PCR (dPCR) result is often based on analysis of a plurality of PCR reactions. A plurality of PCR reactions may be hundreds to thousands of samples. Furthermore, real-time data is collected for each PCR reaction of a sample of the plurality of samples. The number of amplification curves displayed in a single plot makes it difficult to visualize any single amplification curve. To facilitate visualization and analysis, various embodiments include histograms of $C_q$ values displayed alongside or aligned with the corresponding plot of the plurality of real time amplification curves to distinguish amplifications from low and non-amplifications. In a histogram, amplified samples with one or more copies segregate into their respective peaks of the histogram and will be distinct from non-amplification peaks. For example, copy 1, copy 2, and copy 3 may segregate into distinct peaks to show copy number variation. In other words, non-amplified samples may segregate into a single peak at the maximum cycle of PCR. Furthermore, from a histogram plot, $C_q$ ranges may be visualized for amplified samples and non-amplified samples. It should be recognized that quantification cycle may also be referred to, but not limited to, as a threshold cycle ($C_T$ or $C_{RT}$) or crossing point ($C_P$).

Figure 11:
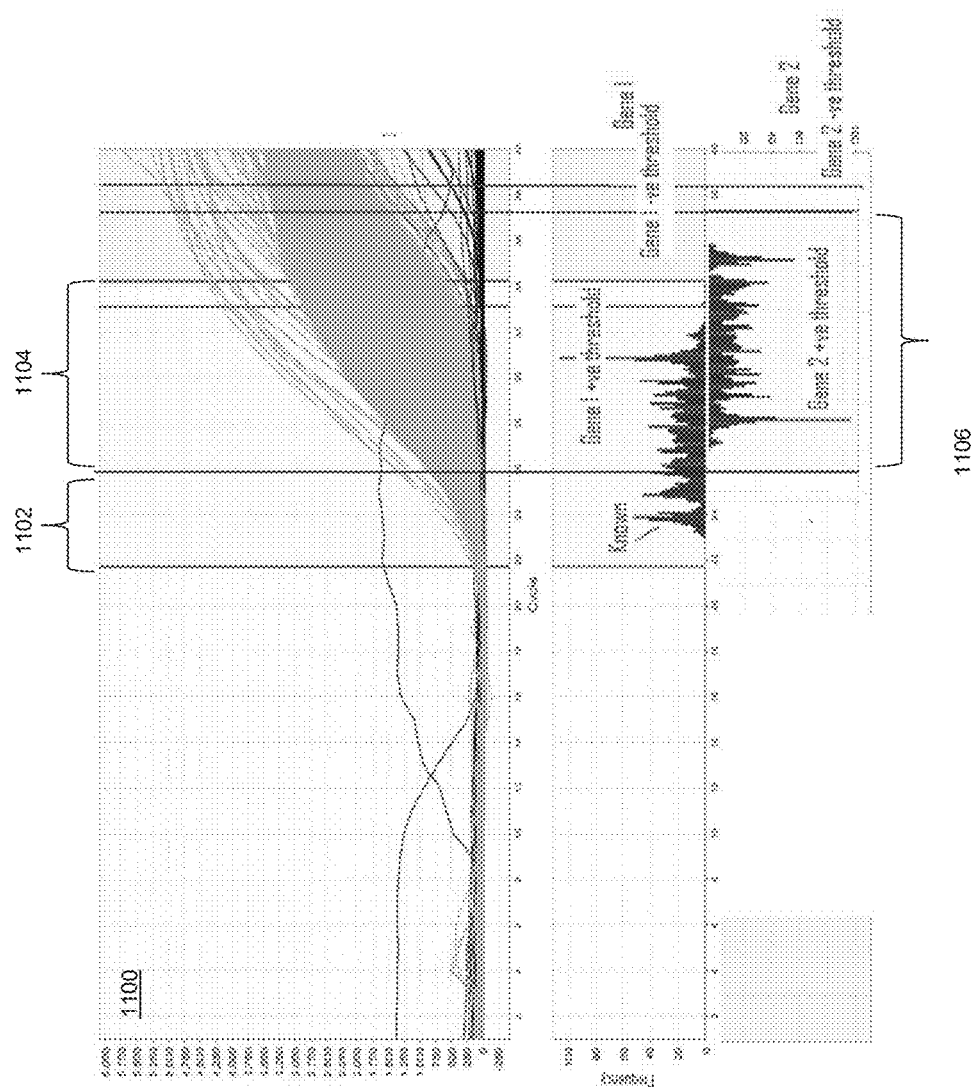
FIG. 11 illustrates another example of an exemplary amplification plot and a corresponding histogram according to various embodiments described herein.

According to various embodiments described herein, results of a dPCR experiment using control samples with known copy number/concentration may be segregated into respective peaks. As such, the histogram in accordance with various embodiments can be used to visualize the control peak compared with unknown peaks. FIG. 11 illustrates a region selected where peaks with a known copy number is visualized and expected. Thus, unknown peaks can be compared with the known peaks.

According to various embodiments described herein, a first histogram may be displayed on an axis and a second histogram may be displayed on the other side of the same axis. In other embodiments, the second histogram may be displayed adjacent to the first histogram. In some embodiments, the second histogram may be displayed in a different color than the first histogram. Further, the visualization may include more than one target. Each target may be displayed in a different color for ease of identification by the user.

With reference to FIG. 11, plot 1100 includes a plurality of amplification curves of two different targets. The selected region 1104 shows the positive amplifications a first target. The region 1106 shows the positive amplifications of a second target. In other words, a plurality of amplification curves for a plurality of targets may be displayed together. According to embodiments described herein, the positive amplifications for each target may be compared by using histograms. Further, the negative amplifications may also be displayed. Thus, embodiments of the present teachings may be utilized in multiplex systems as well as singleplex systems.

In yet other embodiments described herein, filters or a cascade of filters may be used to help a user visualize the data from a plurality of samples. In some embodiments, a user may select a predetermined filter for the data to display for the user on a user interface. In other embodiments, the user may select samples out of the plurality of samples to display on the user interface. In some embodiments, the data selected by the user is emphasized on the display by a different color, for example. Furthermore, the unselected data may still be visualized, but not emphasized. For example, the selected data may be displayed to the user on the user interface in red, while the unselected data is shown in light gray. In this way, the selected data is highlighted from the unselected data for the user.

Computer-Implemented System

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

FIG. 1 is a block diagram that illustrates a computer system 100 that may be employed to carry out processing functionality, according to various embodiments. Instruments to perform experiments may be connected to the exemplary computing system 100. According to various embodiments, the instruments that may be utilized are a thermal cycler system 200 of FIG. 2 or a thermal cycler system 300 of FIG. 3 may utilize. Computing system 100 can include one or more processors, such as a processor 104. Processor 104 can be implemented using a general or special purpose processing engine such as, for example, a microprocessor, controller or other control logic. In this example, processor 104 is connected to a bus 102 or other communication medium.

Further, it should be appreciated that a computing system 100 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 100 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 200 may be configured to connect to one or more servers in a distributed network. Computing system 200 may receive information or updates from the distributed network. Computing system 200 may also transmit information to be stored within the distributed network that may be accessed by other clients connected to the distributed network.

Computing system 100 may include bus 102 or other communication mechanism for communicating information, and processor 104 coupled with bus 102 for processing information.

Computing system 100 also includes a memory 106, which can be a random access memory (RAM) or other dynamic memory, coupled to bus 102 for storing instructions to be executed by processor 104. Memory 106 also may be used for storing temporary variables or other intermediate information during execution of instructions to be executed by processor 104. Computing system 100 further includes a read only memory (ROM) 108 or other static storage device coupled to bus 102 for storing static information and instructions for processor 104.

Computing system 100 may also include a storage device 110, such as a magnetic disk, optical disk, or solid state drive (SSD) is provided and coupled to bus 102 for storing information and instructions. Storage device 110 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 110 may include other similar instrumentalities for allowing computer programs or other instructions or data to be loaded into computing system 100. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 110 to computing system 100.

Computing system 100 can also include a communications interface 118. Communications interface 118 can be used to allow software and data to be transferred between computing system 100 and external devices. Examples of communications interface 118 can include a modem, a network interface (such as an Ethernet or other NIC card), a communications port (such as for example, a USB port, a RS-232C serial port), a PCMCIA slot and card, Bluetooth, etc. Software and data transferred via communications interface 118 are in the form of signals which can be electronic, electromagnetic, optical or other signals capable of being received by communications interface 118. These signals may be transmitted and received by communications interface 118 via a channel such as a wireless medium, wire or cable, fiber optics, or other communications medium. Some examples of a channel include a phone line, a cellular phone link, an RF link, a network interface, a local or wide area network, and other communications channels.

Computing system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104, for example. An input device may also be a display, such as an LCD display, configured with touchscreen input capabilities. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A computing system 100 provides data processing and provides a level of confidence for such data. Consistent with certain implementations of embodiments of the present teachings, data processing and confidence values are provided by computing system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 104 for execution. Such instructions, generally referred to as "computer program code" (which may be grouped in the form of computer programs or other groupings), when executed, enable the computing system 100 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computing system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

PCR Instruments

Figure 2:
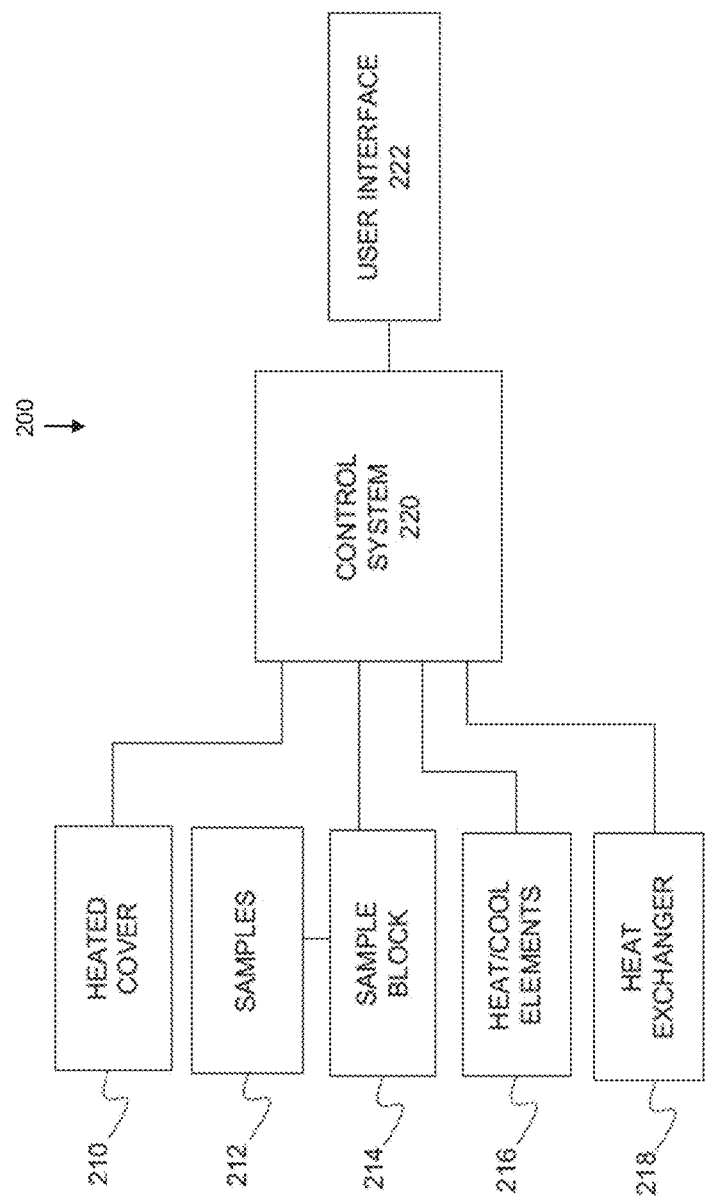
FIG. 2 is a block diagram that illustrates a polymerase chain reaction (PCR) instrument, upon which embodiments of the present teachings may be implemented.

As mentioned above, an instrument that may be utilized according to various embodiments, but is not limited to, is a polymerase chain reaction (PCR) instrument. FIG. 2 is a block diagram that illustrates a PCR instrument 200, upon which embodiments of the present teachings may be implemented. PCR instrument 200 may include a heated cover 210 that is placed over a plurality of samples 212 contained in a sample support device (not shown). In various embodiments, a sample support device may be a glass or plastic slide with a plurality of sample regions, which sample regions have a cover between the sample regions and heated cover 210. Some examples of a sample support device may include, but are not limited to, a multi-well plate, such as a standard microtiter 96-well, a 384-well plate, or a microcard, or a substantially planar support, such as a glass or plastic slide. The sample regions in various embodiments of a sample support device may include depressions, indentations, ridges, and combinations thereof, patterned in regular or irregular arrays formed on the surface of the substrate. Various embodiments of PCR instruments include a sample block 214, elements for heating and cooling 216, a heat exchanger 218, control system 220, and user interface 222. Various embodiments of a thermal block assembly according to the present teachings comprise components 214-218 of PCR instrument 200 of FIG. 2.

For embodiments of PCR instrument 200 in FIG. 2, control system 220, may be used to control the functions of the detection system, heated cover, and thermal block assembly. Control system 220 may be accessible to an end user through user interface 222 of PCR instrument 200 in FIG. 2. Also a computer system 100, as depicted in FIG. 1, may serve as to provide the control the function of PCR instrument 200 in FIG. 2, as well as the user interface function. Additionally, computer system 100 of FIG. 1 may provide data processing, display and report preparation functions. All such instrument control functions may be dedicated locally to the PCR instrument, or computer system 100 of FIG. 1 may provide remote control of part or all of the control, analysis, and reporting functions, as will be discussed in more detail subsequently.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

As described above, various embodiments described herein are for visualizing a sample-target group. Also mentioned above, gathering useful information from an amplification plot of a plurality of samples is difficult. In other words, distinguishing a desired amplification curve from a large number of amplification curves on a single plot is challenging. As such, analyzing and assessing the data for useful results is also challenging.

Histograms

According to various embodiments described herein, a histogram may show the distribution of quantification cycles ($C_q$). However, from only the histogram, it may be difficult to determine the amplified samples with possibly non-amplified samples. It should be recognized that quantification cycle may also be referred to, but not limited to, as a threshold cycle ($C_T$ or $C_{RT}$) or crossing point ($C_P$).

Figure 3:
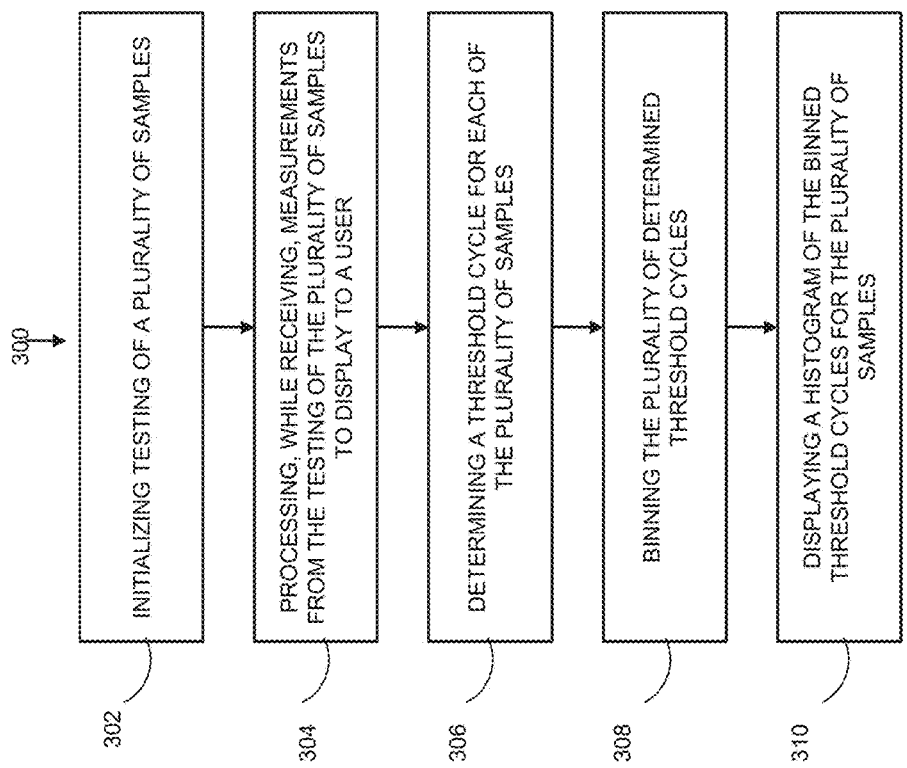
FIG. 3 is a flowchart illustrating an exemplary method according to various embodiments of the present teachings.

FIG. 3 is a flowchart illustrating an exemplary method 300 for displaying a visualization of data. As described above, steps described may be performed by a processor executing instructions. In step 302, the processor initializes testing of a plurality of samples. In step 304, the method includes processing, while receiving, measurements from the testing of the plurality of samples to display to a user. Next, in step 306, a quantification cycle is determined for each of the plurality of samples. The determined quantification cycles of the samples are binned in step 308. Finally, in step 301, a histogram of the binned quantification cycles are displayed.

Figures 4A, 4B:
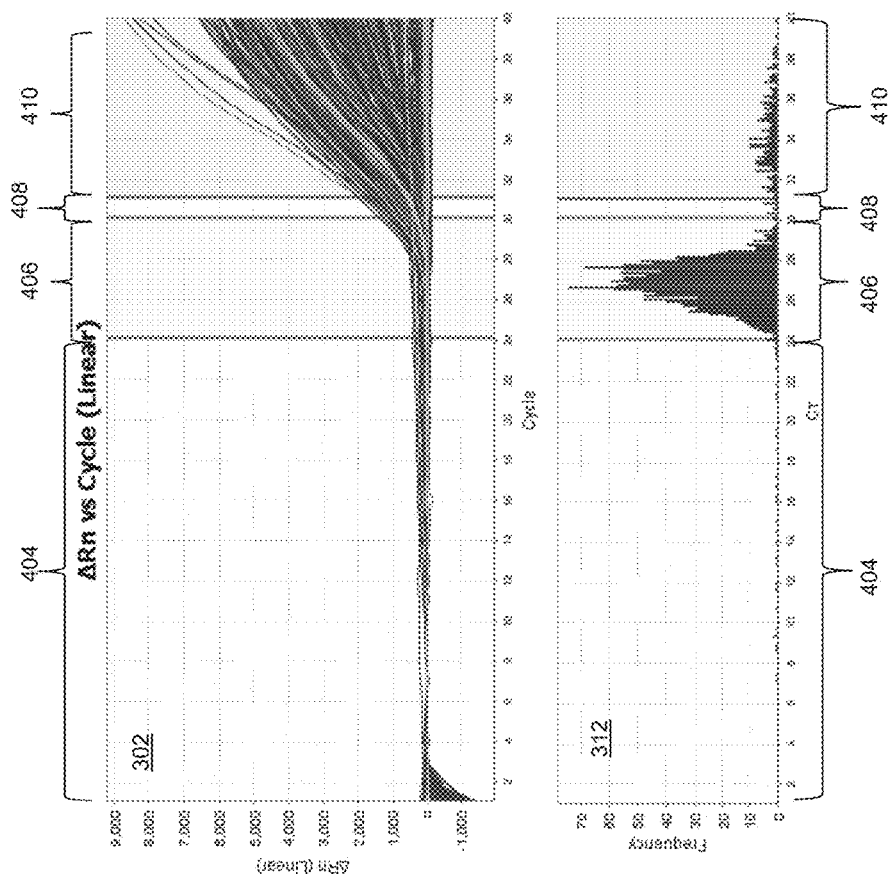
FIG. 4A illustrates an exemplary amplification plot according to various embodiments described herein.
FIG. 4B illustrates a corresponding histogram plot according to various embodiments described herein.

FIG. 4A illustrates an amplification plot 402 showing a plurality of amplification curves of a plurality of samples.

FIG. 4B illustrates a histogram 412 of a plurality of quantification cycle values of the plurality of samples that corresponds to amplification plot 402. The x-axis of both amplification plot 402 and histogram 412 shows the number of amplification cycles. The y-axis of amplification plot 402 shows $\Delta R_n$ the difference between the normalized reporter fluorescent signal and the baseline fluorescent signal. $\Delta R_n$ indicates the magnitude of fluorescent signal by PCR. The y-axis of histogram 412 is the frequency of samples with a particular quantification cycle ($C_q$).

According to various embodiments, amplification plot 402 may be displayed alongside histogram 412 such that corresponding regions may be viewed by the user easily. For example, regions 404, 406, 408, and 410 are shown in both amplification plot 402 and histogram 412. In some embodiments, the amplification plot 402 and histogram 412 are displayed on a user interface in positions so that the corresponding regions are displayed in a way for a user to easily compare the regions. For example, a corresponding region of histogram 412 may be displayed directly below the region of the amplification plot. A user may select particular regions to be highlighted in some embodiments. These ranges are draggable and correspond to same cycles values in the histogram plot and amplification plot. Furthermore, selection can be performed either in amplification plot or histogram. In other embodiments, the processor may automatically select regions to be highlighted to the user.

In the examples shown in FIGS. 4A and 4B, PCR results of a plurality of samples is shown. By examining histogram 412, it can be seen that a few samples amplified before cycle 24. However, it can be seen in amplification plot 402 that there is no true amplification before cycle 24. As such, a user may determine that the samples that have quantification cycles before cycle 24 are not true sample amplifications or if there is low amplifications.

Figure 10:
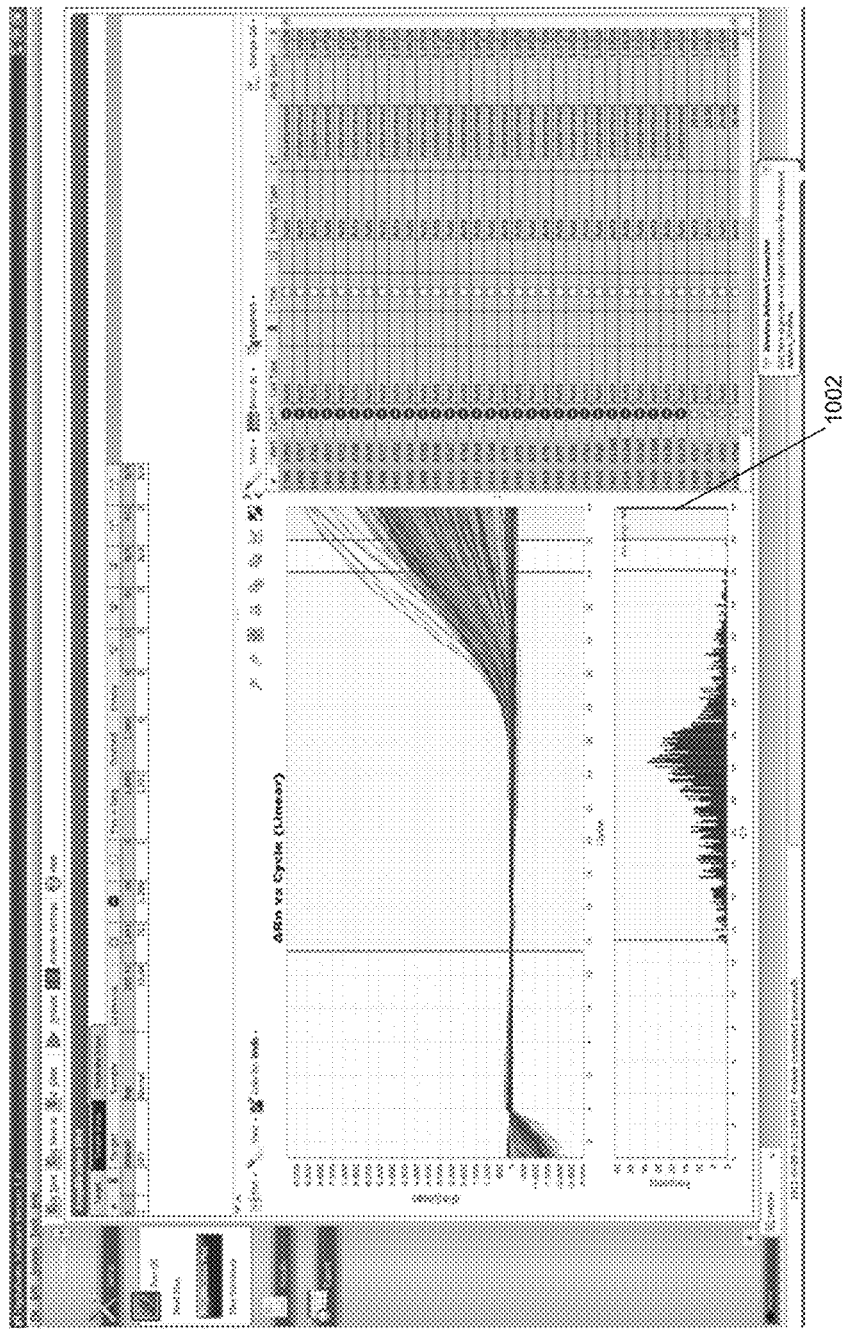
FIG. 10 illustrates another example of an exemplary amplification plot and a corresponding histogram according to various embodiments described herein.

As another example, FIG. 10 depicts an exemplary histogram alongside a corresponding amplification plot. In this example, an indication 1002 of no amplification at cycle 40. In this example, indication 1002 is shown by a colored bar.

Furthermore, a user may be able to visualize peaks and distributions of quantification cycle values in the group including a plurality of samples. In this way, the user may be able to visualize whether a quantification cycle includes positive amplifications or negative amplifications. Furthermore, thresholds such as positive $C_q$, maximum positive $C_q$, minimum negative $C_q$, maximum negative $C_q$ may be used to establish ranges for true amplification versus undetermined amplifications versus non-amplifications.

Cascading Filters

In other embodiments of the present teachings, a plurality of experiments may be displayed, represented and summarized at a top-level by a variety of categories or grouping mechanisms. In various embodiments described herein, a dataset may be grouped by individual attributes of the data, such as assay, sample or experiment. Furthermore, in other embodiments, the dataset may be grouped by compound or combined attributes, such as target-sample or target-sample-dilution. These data groupings allow the user to organize, sort and survey their data at a high-level across the entire dataset. The nature of this high-level grouping for a dataset is arbitrary. Whereas, the specific groupings for an application are defined by the scientific domain that the software is designed to support. According to various embodiments, filters may be cascaded so that the user may be able to visualize the large number of results in a useful manner.

As the user surveys or scrolls through a given dataset, embodiments described herein provide additional filtered views of the dataset to enable further investigation of details, attributes, characteristics and relationships of relevant subgroups within the dataset. Selection of one or more high-level groups provides additional detailed data displays of subgroups of data. This pattern can be repeated down to the most atomic level of the data within the dataset. Subgroup displays can include tabular lists of data; graphic visualizations, such as charts, graphs, heat maps, plots, as well as various articulations in the UI display for unselected, excluded or omitted data.

As the user continues to investigate the dataset, or subgroups within the dataset, selection of individual data elements at any subgroup level further filters the displayed data and visualizations in its lower subgroup displays.

Moreover, embodiments of the present teaching allow the user to bookmark, select or omit data within a subgroup, as well as apply manual settings or overrides to the data at varying levels or subgroups.

Figure 5:
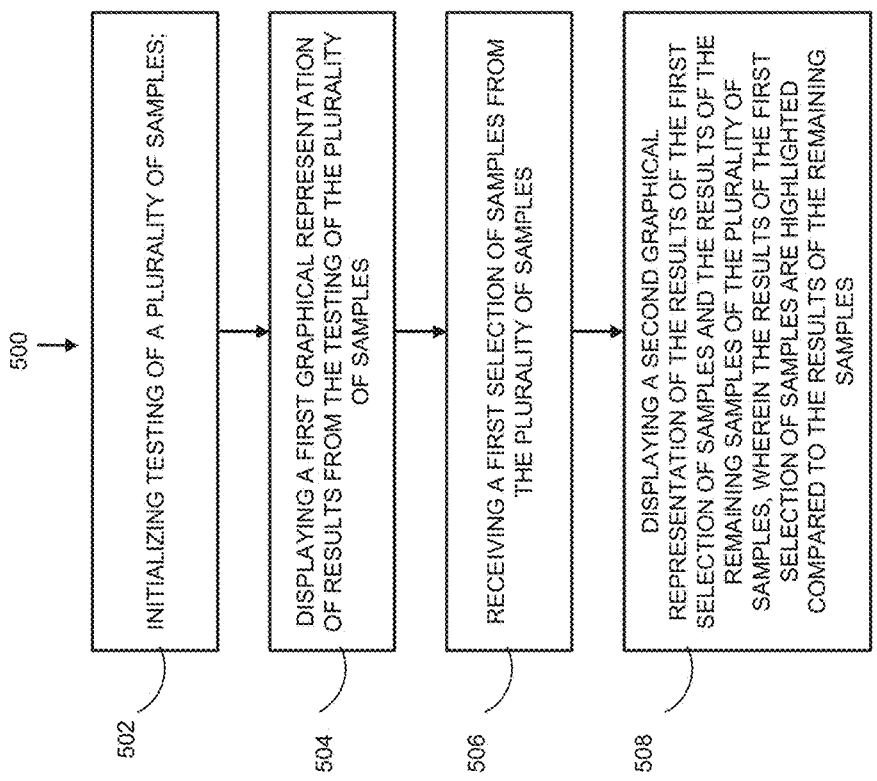
FIG. 5 is a flowchart illustrating an exemplary method according to various embodiments of the present teachings.

FIG. 5 illustrates a flowchart depicting an exemplary method 500 for displaying filtered results. In step 502, the processor initializes testing of a plurality of samples. In step 504, the method includes displaying a first graphical representation of results from the testing of the plurality of samples. In step 506, a first selection of samples from the plurality of samples is received. A second graphical representation of the result of the first selection of samples and the results of the remaining samples of the plurality of samples, in step 508. The results of the first selection of samples are highlighted compared to the results of the remaining samples. According to various embodiments, the selected samples are shown in a color while the remaining samples are shown in a muted color.

Figure 6:
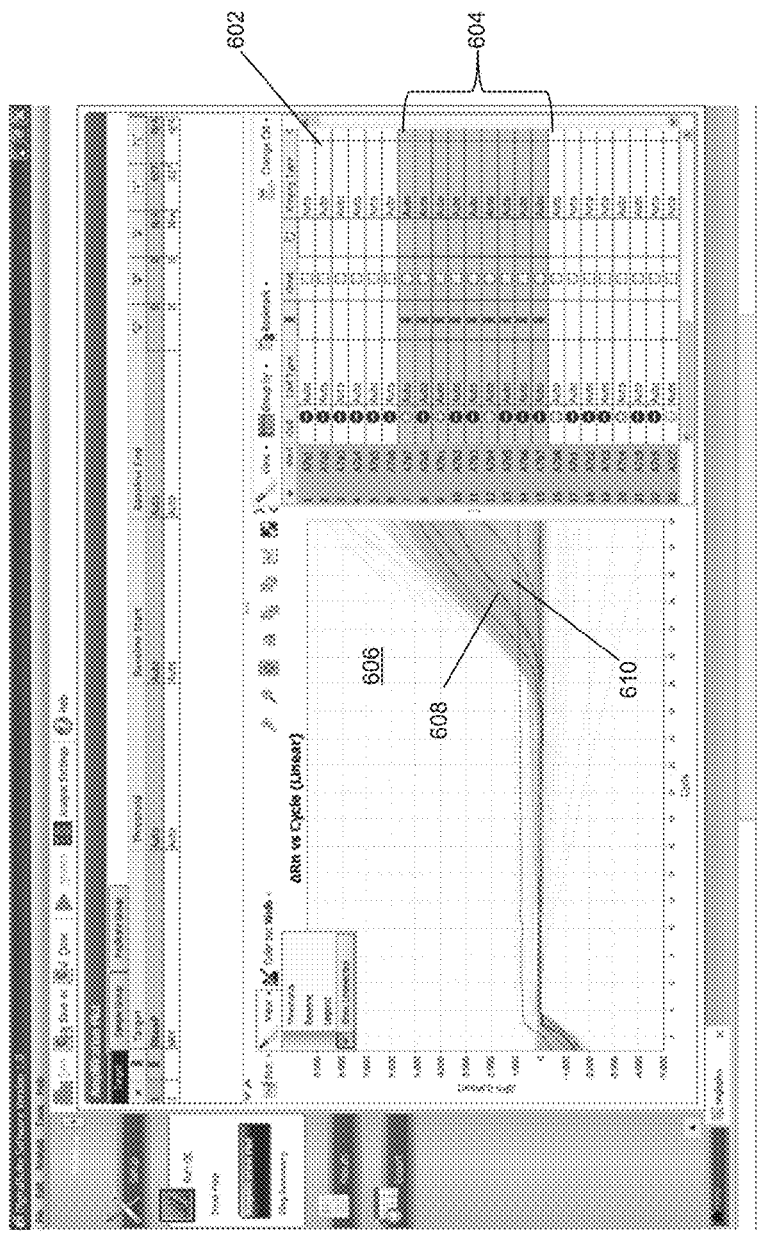
FIG. 6 illustrates an example of a filtered plot view according to various embodiments described herein.

FIG. 6 depicts, according to various embodiments, a selection 604 of RNaseP Target (high-level group), with summarized data, with subgroup data displays of results table 602 and amplification plot 606. A selection 604 of several samples in various wells have been bookmarked in the results table 602. The selection 604 is reflected on amplification plot. For example, a selected sample is reflected as the selected amplification curve 608. Moreover, unselected wells are also displayed in the background on the amplification plot 606, such as unselected amplification curve 610.

Figure 7:
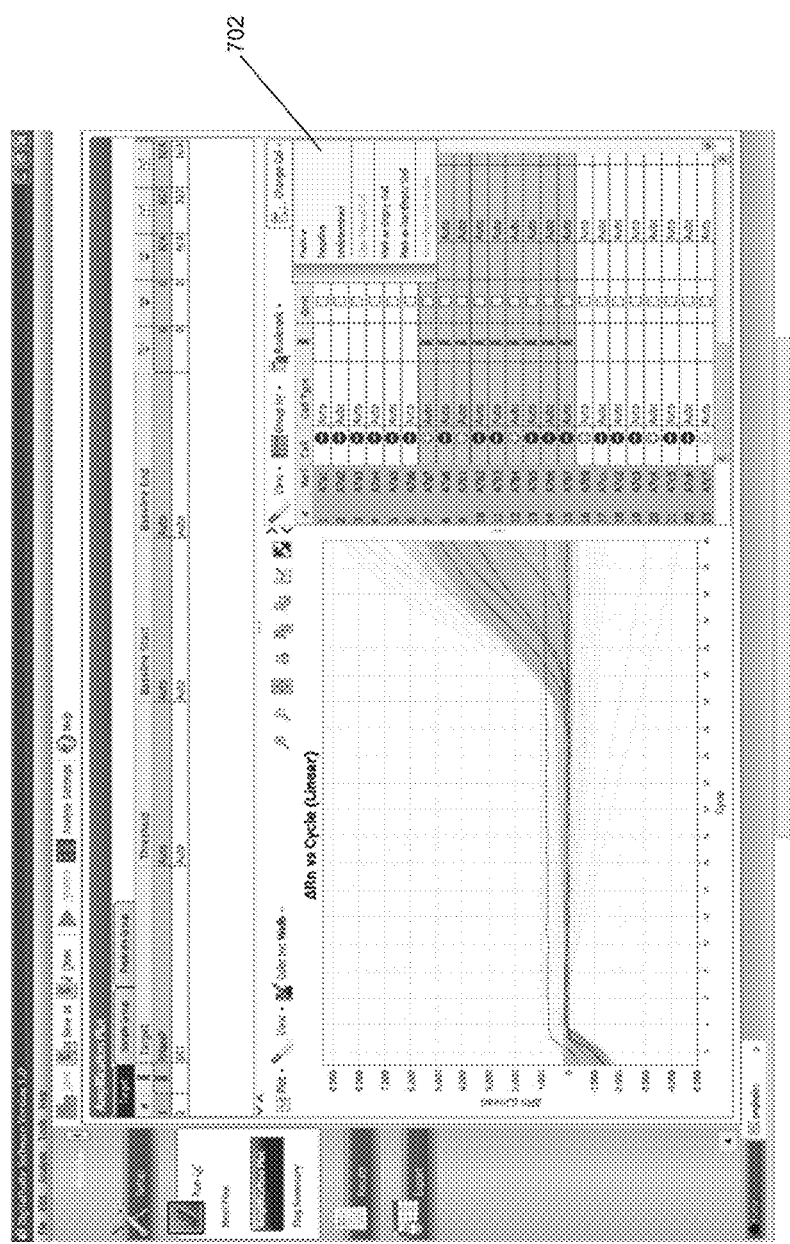
FIG. 7 illustrates another example of a filtered plot view according to various embodiments described herein.

With reference to FIG. 7, according to various embodiments, a user may manually override a determination of data within a subgroup that was generated or calculated by the processor. For example, a processor may automatically determine if an amplification of a sample is a negative or low amplification. However, a user may select menu 702 to manually override the negative amplification or low amplification determination to a positive amplification determination.

Figure 8:
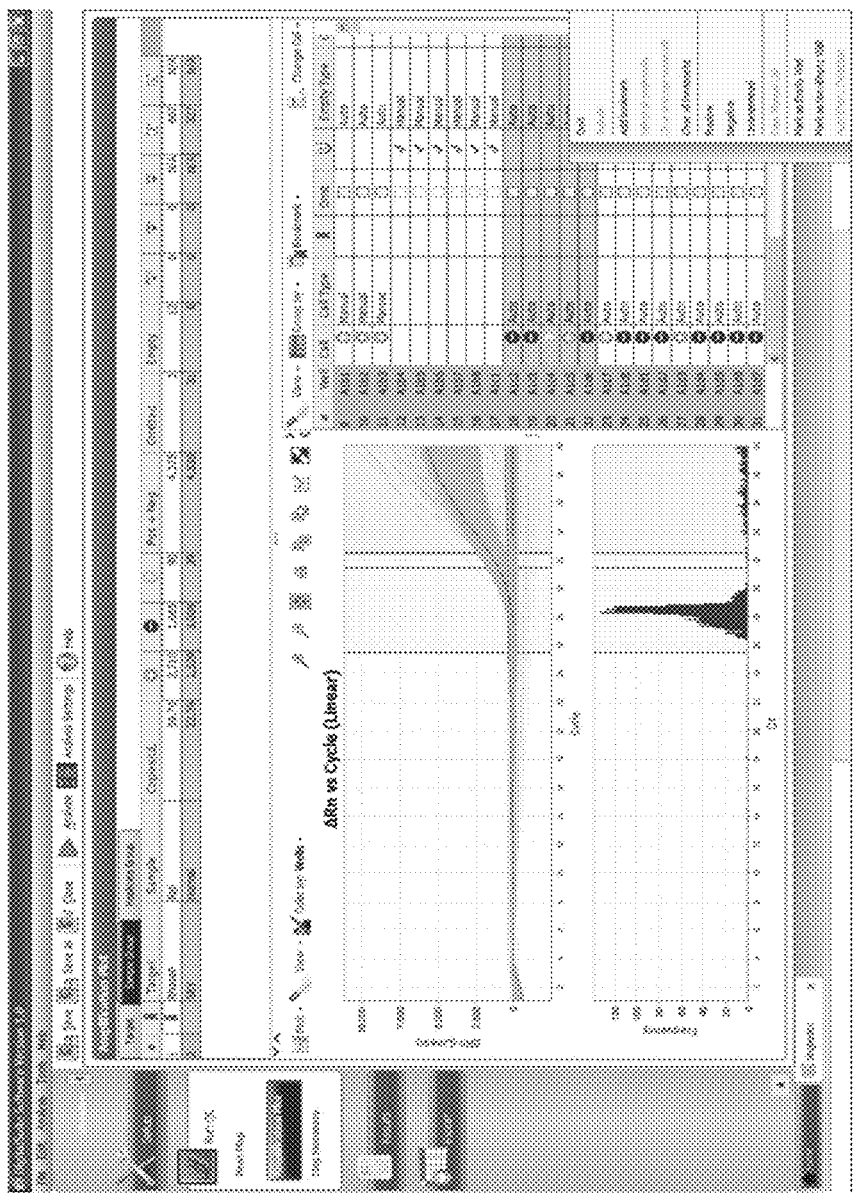
FIG. 8 illustrates another example of a filtered plot view according to various embodiments described herein.

FIG. 8 shows high-level grouping of dataset by compound attributes of the target sample with summary data elements. Filtered subgroups show individual data selected, manually overridden, synchronized data display on the visualization provided to a user. Moreover, contextual relevance for the selected data is illustrated by showing unselected wells in the background. Earlier selections from other subgroups (see FIG. 7) may be retained, as well as indicated in its top-level group.

Figure 9:
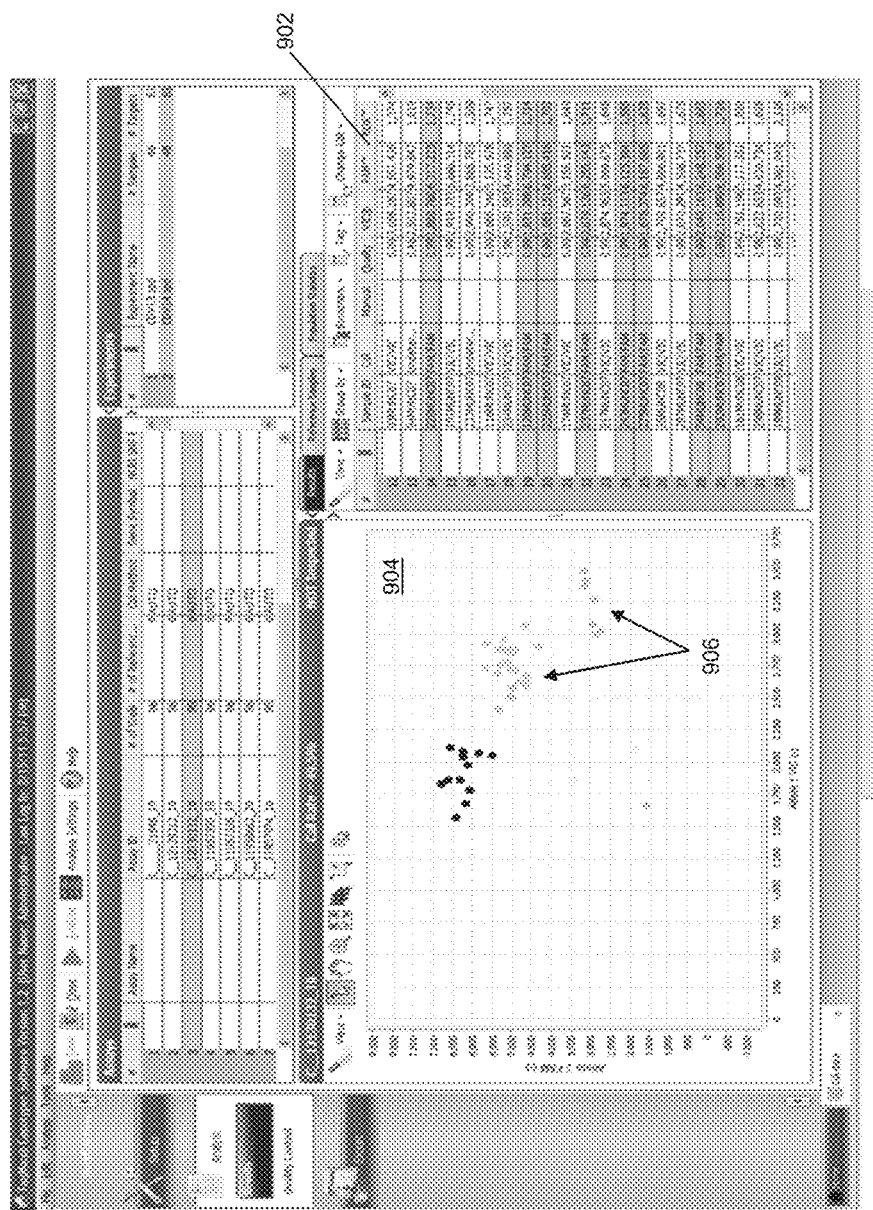
FIG. 9 illustrates yet another example of a filtered plot view according to various embodiments described herein.

According to various embodiments described herein, FIG. 9 depicts top-level grouping by assay, where the selected assay displays filtered subgroup by experiment. Selected experiment displays filtered subgroup by experiment in well results table 902. Selected wells further may be displayed prominently on scatter plot 904, with unselected wells 906 displayed in the background of the plot.

Therefore, according to the above, some examples of the disclosure comprise the following:

In another example, a computer-implemented method of generating a digital polymerase chain reaction (dPCR) result is provided. The method comprises detecting a first set of emission data from a plurality of samples, each included in a sample region of a plurality of sample regions, at a first time during an amplification period; determining a positive or negative amplification determination for each sample of the plurality of samples based in part on the first set of emission data; and generating a dPCR result based on the positive or negative amplification determinations for the plurality of samples.

Additionally or alternatively, in one or more of the examples disclosed above, the method may further comprise detecting a second set of emission data from the plurality of samples at a second time during an amplification period, wherein the first and second set of emission data is included in amplification curve data for each of the plurality of samples.

Additionally or alternatively, in one or more of the examples disclosed above, the method may further comprise detecting emission data from the plurality of samples after each stage of thermal cycling in the amplification period to generate the amplification curve data.

Additionally or alternatively, in one or more of the examples disclosed above, the method further comprise detecting real-time emission data during the amplification period to generate the amplification curve data.

Additionally or alternatively, in one or more of the examples disclosed above, determining the positive or negative amplification determination for each sample of the plurality of samples comprises: determining a quantification cycle for each of the plurality of samples; binning the plurality of determined quantification cycles; and displaying a histogram of the binned quantification cycles for the plurality of samples.

Additionally or alternatively, in one or more of the examples disclosed above, the method further comprises determining a valid testing of a sample in the plurality of samples based on the amplification curve data of the sample.

Additionally or alternatively, in one or more of the examples disclosed above, the method further comprises displaying to the user the amplification curve data and the positive or negative determinations.

Additionally or alternatively, in one or more of the examples disclosed above, the amplification curve data is displayed along with the histogram to the user.

Additionally or alternatively, in one or more of the examples disclosed above, a quantification cycle lower than a predetermined threshold is determined to be an invalid testing.

Additionally or alternatively, in one or more of the examples disclosed above, a quantification cycle higher than a predetermined threshold is determined to be a valid testing.

Additionally or alternatively, in one or more of the examples disclosed above, a quantification cycle within a predetermined range is determined to be a valid testing.

In another example, a computer-readable medium encoded with instructions, executable by a processor is provided. The instructions comprise instructions for: detecting a first set of emission data from a plurality of samples, each included in a sample region of a plurality of sample regions, at a first time during an amplification period; detecting a second set of emission data from the plurality of samples at a second time during an amplification period, wherein the first and second set of emission data is included in amplification curve data for each of the plurality of samples; determining a positive or negative amplification determination for each sample of the plurality of samples based in part on the corresponding amplification curve data; and generating a dPCR result based on the positive or negative amplification determinations for the plurality of samples.

Additionally or alternatively, in one or more of the examples disclosed above, the instructions for determining the positive or negative amplification determination for each sample of the plurality of samples comprises instructions for: determining a quantification cycle for each of the plurality of samples; binning the plurality of determined quantification cycles; and displaying a histogram of the binned quantification cycles for the plurality of samples.

Additionally or alternatively, in one or more of the examples disclosed above, the computer-readable medium further comprises instructions for: determining a valid testing of a sample in the plurality of samples based on the amplification curve data of the sample.

Additionally or alternatively, in one or more of the examples disclosed above, the instructions further comprise instructions for displaying to the user the amplification curve data and the positive or negative determinations.

Additionally or alternatively, in one or more of the examples disclosed above, the amplification curve data is displayed along with the histogram to the user.

Additionally or alternatively, in one or more of the examples disclosed above, a quantification cycle lower than a predetermined threshold is determined to be an invalid testing.

Additionally or alternatively, in one or more of the examples disclosed above, a quantification cycle higher than a predetermined threshold is determined to be a valid testing.

Additionally or alternatively, in one or more of the examples disclosed above, a quantification cycle within a predetermined range is determined to be a valid testing.

In another example, a system for generating a digital polymerase chain reaction result (dPCR) is provided. The system comprises a thermal cycler for performing amplification on a plurality of samples; a processor; and a memory encoded with instructions for: detecting a first set of emission data from a plurality of samples, each included in a sample region of a plurality of sample regions, at a first time during an amplification period; detecting a second set of emission data from the plurality of samples at a second time during an amplification period, wherein the first and second set of emission data is included in amplification curve data for each of the plurality of samples; determining a positive or negative amplification determination for each sample of the plurality of samples based in part on the corresponding amplification curve data; and generating a dPCR result based on the positive or negative amplification determinations for the plurality of samples.

Additionally or alternatively, in one or more of the examples disclosed above, the system further comprises detecting emission data from the plurality of samples after each stage of thermal cycling in the amplification period to generate the amplification curve data.

Additionally or alternatively, in one or more of the examples disclosed above, the system further comprises instructions for detecting real-time emission data during the amplification period to generate the amplification curve data.

Additionally or alternatively, in one or more of the examples disclosed above, the determining the positive or negative amplification determination for each sample of the plurality of samples comprises: determining a quantification cycle for each of the plurality of samples; binning the plurality of determined quantification cycles; and displaying a histogram of the binned quantification cycles for the plurality of samples.

Additionally or alternatively, in one or more of the examples disclosed above, the system further comprises instructions for determining a valid testing of a sample in the plurality of samples based on the amplification curve data of the sample.

Additionally or alternatively, in one or more of the examples disclosed above, the system further comprising instructions for displaying to the user the amplification curve data and the positive or negative determinations.

Additionally or alternatively, in one or more of the examples disclosed above, the amplification curve data is displayed along with the histogram to the user.

Additionally or alternatively, in one or more of the examples disclosed above, a quantification cycle lower than a predetermined threshold is determined to be an invalid testing.

Additionally or alternatively, in one or more of the examples disclosed above, a quantification cycle higher than a predetermined threshold is determined to be a valid testing.

Additionally or alternatively, in one or more of the examples disclosed above, a quantification cycle within a predetermined range is determined to be a valid testing.

In another example, a computer-implemented method for visualizing a plurality of data plots is provided. The method comprises: initializing testing of a plurality of samples; processing, while receiving, measurements from the testing of the plurality of samples to display to a user; determining a quantification cycle for each of the plurality of samples; binning the plurality of determined quantification cycles; and displaying a histogram of the binned quantification cycles for the plurality of samples.

Additionally or alternatively, in one or more of the examples disclosed above, the computer-implemented method further comprises determining a valid testing of a sample in the plurality of samples based on the histogram.

Additionally or alternatively, in one or more of the examples disclosed above, the measurements from the testing of the plurality of samples are displayed to the user as a plurality of amplification curves.

Additionally or alternatively, in one or more of the examples disclosed above, the plurality of amplification curves is displayed along with the histogram to the user.

Additionally or alternatively, in one or more of the examples disclosed above, a quantification cycle lower than a predetermined threshold is determined to be an invalid testing.

Additionally or alternatively, in one or more of the examples disclosed above, a quantification cycle higher than a predetermined threshold is determined to be a valid testing.

Additionally or alternatively, in one or more of the examples disclosed above, a quantification cycle within a predetermined range is determined to be a valid testing.

In another example, a computer-readable medium encoded with instructions, executable by a processor is provided. The instructions comprise instructions for: initializing testing of a plurality of samples; processing, while receiving, measurements from the testing of the plurality of samples to display to a user; determining a Cq for each of the plurality of samples; binning the plurality of determined quantification cycles; and displaying a histogram of the binned quantification cycles for the plurality of samples.

Additionally or alternatively, in one or more of the examples disclosed above, the instructions further comprise instructions for: determining a valid testing of a sample in the plurality of samples based on the histogram.

Additionally or alternatively, in one or more of the examples disclosed above, the measurements from the testing of the plurality of samples are displayed to the user as a plurality of amplification curves.

Additionally or alternatively, in one or more of the examples disclosed above, the plurality of amplification curves is displayed along with the histogram to the user.

Additionally or alternatively, in one or more of the examples disclosed above, a quantification cycle lower than a predetermined threshold is determined to be an invalid testing.

Additionally or alternatively, in one or more of the examples disclosed above, a quantification cycle higher than a predetermined threshold is determined to be a valid testing.

Additionally or alternatively, in one or more of the examples disclosed above, a quantification cycle within a predetermined range is determined to be a valid testing.

In another example, a system for visualizing a plurality of data plots is provided. The system comprises: a processor; and a memory encoded with instructions for: initializing testing of a plurality of samples; processing, while receiving, measurements from the testing of the plurality of samples to display to a user; determining a quantification cycle for each of the plurality of samples; binning the plurality of determined quantification cycles; and displaying a histogram of the binned quantification cycles for the plurality of samples.

Additionally or alternatively, in one or more of the examples disclosed above, the instructions further include instructions for: determining a valid testing of a sample in the plurality of samples based on the histogram.

Additionally or alternatively, in one or more of the examples disclosed above, the measurements from the testing of the plurality of samples are displayed to the user as a plurality of amplification curves.

Additionally or alternatively, in one or more of the examples disclosed above, the plurality of amplification curves is displayed along with the histogram to the user.

Additionally or alternatively, in one or more of the examples disclosed above, a quantification cycle lower than a predetermined threshold is determined to be an invalid testing.

Additionally or alternatively, in one or more of the examples disclosed above, a quantification cycle higher than a predetermined threshold is determined to be a valid testing.

Additionally or alternatively, in one or more of the examples disclosed above, a quantification cycle within a predetermined range is determined to be a valid testing.

In another example, a computer-implemented method for visualizing a plurality of data plots is provided. The method comprises: initializing testing of a plurality of samples; displaying a first graphical representation of results from the testing of the plurality of samples; receiving a first selection of samples from the plurality of samples; and displaying a second graphical representation of the results of the first selection of samples and the results of the remaining samples of the plurality of samples, wherein the results of the first selection of samples are highlighted compared to the results of the remaining samples.

Additionally or alternatively, in one or more of the examples disclosed above, the first selection of samples are highlighted by a color.

Additionally or alternatively, in one or more of the examples disclosed above, the computer-implemented method further comprises: receiving a second selection of samples, based on the first selection of samples; and displaying a third graphical representation of the results of the second selection of samples and the results of the remaining samples of the plurality of samples, wherein the results of the second selection of samples are highlighted compared to the results of the remaining samples.

Additionally or alternatively, in one or more of the examples disclosed above, the first selection of samples is dynamically determined based on a characteristic of a sample.

Additionally or alternatively, in one or more of the examples disclosed above, the first selection of samples is dynamically determined based on a characteristic of the result of each sample of the plurality of samples.

Although various embodiments have been described with respect to certain exemplary embodiments, examples, and applications, it will be apparent to those skilled in the art that various modifications and changes may be made without departing from the present teachings.

What is claimed is:

1. A computer-implemented method of operating an emission analysis system to generate a digital polymerase chain reaction (dPCR) result, the method comprising:
   at a first time of an amplification process, utilizing light sensors of a PCR instrument to generate a first set of emission readings from a plurality of samples;
   at a second time of the amplification process, utilizing the light sensors to generate a second set of emission readings from the plurality of samples, wherein the first set of emission readings and the second set of emission readings are used to generate both quantitative polymerase chain reaction (qPCR) results and a dPCR result from the amplification process of a sample of the plurality of samples;
   operating a processor programmed to:
      determine amplification curve values for the sample of the plurality of samples from the first and second sets of emission readings;
      determine a quantification cycle for the sample of the plurality of samples;
      determine a positive amplification or a negative amplification for the sample of the plurality of samples based in part on the amplification curve values;
      generate the dPCR result based on the amplification determinations for the sample of the plurality of samples; and
      for the sample of the plurality of samples, use amplification curve values obtained for the sample to facilitate validation of the dPCR result.

2. The computer-implemented method of claim 1, further comprising: for each cycle of the amplification process, utilizing the light sensors to detect emissions from the sample of the plurality of samples to generate the amplification curve values.

3. The computer-implemented method of claim 1, further comprising: operating the light sensors to detect real-time emissions during the amplification process to generate the amplification curve values.

4. The computer-implemented method of claim 1, wherein determining the positive or negative amplification determination for the sample of the plurality of samples comprises:

binning a plurality of determined quantification cycles for the sample of the plurality of samples to generate a plurality of binned quantification cycles; and generating on the machine display a histogram of the binned quantification cycles for the sample of the plurality of samples.

5. The computer-implemented method of claim 1, further comprising:

determining a valid testing of a particular sample in the plurality of samples based on amplification curve values of the particular sample.

6. The computer-implemented method of claim 1, further comprising: operating the processor to generate on the machine display the amplification curve values and the positive or negative determinations.

7. The computer-implemented method of claim 4, wherein the amplification curve values are generated on the machine display along with the histogram.

8. The computer-implemented method of claim 4, further comprising:

operating the processor to indicate that the quantification cycle being lower than a predetermined threshold indicates an invalid testing.

9. The computer-implemented method of claim 4, further comprising:

operating the processor to indicate that the quantification cycle being higher than a predetermined threshold indicates a valid testing.

10. The computer-implemented method of claim 4, further comprising:

operating the processor to indicate that the quantification cycle being within a predetermined range indicates a valid testing.

11. A computer-readable medium encoded with instructions, executable by a processor, the instructions to cause the processor to:

at a first time of an amplification process, detect a first set of light emission readings by a PCR instrument from a plurality of samples;

at a second time of the amplification process, detect a second set of light emission readings from the plurality of samples, wherein the first set of light emission readings and the second set of light emission readings are used to generate both quantitative polymerase chain reaction (qPCR) results and a dPCR result from the amplification process of a sample of the plurality of samples;

transform the first and second sets of light emission readings into corresponding amplification curve values for the sample of the plurality of samples, thus forming a plurality of amplification curve values;

determine a positive amplification or a negative amplification for the sample of the plurality of samples based in part on the amplification curve values;

generate the dPCR result based on the amplification determinations for the sample of the plurality of samples; and for the sample of the plurality of samples, use amplification curve values obtained for the sample to facilitate validation of the dPCR result.

12. The computer-readable medium of claim 11, wherein determining the positive or negative amplification determination for the sample of the plurality of samples further comprises:

determining a quantification cycle for the sample of the plurality of samples, thus forming a plurality of determined quantification cycles;

binning the plurality of determined quantification cycles, thus forming binned quantification cycles; and generating on the machine display a histogram of the binned quantification cycles for the sample of the plurality of samples.

13. The computer-readable medium of claim 11 the instructions to cause the processor to further:

output an indication of a valid testing of a particular sample of the plurality of samples based on amplification curve values of the particular sample.

14. The computer-readable medium of claim 11, the instructions to cause the processor to further:

generate on the machine display the amplification curve values and the positive or negative determinations.

15. The computer-readable medium of claim 12, the instructions to cause the processor to further:

display the amplification curve values along with the histogram.

16. The computer-readable medium of claim 12, the instructions to cause the processor to further:

output the indication to indicate that the quantification cycle being lower than a predetermined threshold indicates an invalid testing.

17. The computer-readable medium of claim 12, the instructions to cause the processor to further:

output the indication to indicate that the quantification cycle being higher than a predetermined threshold indicates a valid testing.

18. The computer-readable medium of claim 12, the instructions to cause the processor to further:

output the indication to indicate that the quantification cycle being within a predetermined range indicates a valid testing.

19. A system for analyzing a digital polymerase chain reaction (dPCR), the system comprising:

a thermal cycler for performing amplification on a plurality of samples and using a first set of emissions and a second set of emissions to generate both quantitative polymerase chain reaction (qPCR) results and a dPCR result from the amplification of a sample of the plurality of samples;

a processor; and a memory encoded with instructions to operate a machine processor to:

at a first time of an amplification process, detect the first set of emissions from the plurality of samples;

at a second time of the amplification process, detect the second set of emissions from the plurality of samples;

transform the first and second sets of emissions into amplification curve values for the sample of the plurality of samples;

determine a positive amplification or a negative amplification for the sample of the plurality of samples based in part on the amplification curve values;

generate the dPCR result based on the amplification determinations for the sample of the plurality of samples; and for the sample of the plurality of samples, use amplification curve values obtained for the sample to facilitate validation of the dPCR result.

20. The system of claim 19, further comprising instructions to cause the processor to:

for each cycle of the amplification process, detect emissions from the sample of the plurality of samples to generate an amplification curve.

21. The system of claim 19, further comprising instructions to cause the processor to:
   detect real-time emissions during the amplification process to generate an amplification curve.

22. The system of claim 19, wherein determining the positive or negative amplification determination for the sample of the plurality of samples comprises:
   determining a quantification cycle for the sample of the plurality of samples to generate a plurality of quantification cycles;
   binning the plurality of quantification cycles; and
   generating and displaying on the machine display a histogram of the binned quantification cycles for the sample of the plurality of samples.

23. The system of claim 19, further comprising instructions to cause the processor to:
   determine a valid testing of a particular sample in the plurality of samples based on the corresponding amplification curve values of the particular sample.

24. The system of claim 19, further comprising instructions to cause the processor to:
   generate on the machine display an amplification curve and the positive or negative determinations.

25. The system of claim 22, wherein the amplification curve is displayed along with the histogram.

26. The system of claim 22, further comprising instructions to cause the processor to:
   determine that a quantification cycle lower than a predetermined threshold is an invalid testing.

27. The system of claim 22, further comprising instructions to cause the processor to:
   determine that a quantification cycle higher than a predetermined threshold is a valid testing.

28. The system of claim 22, further comprising instructions to cause the processor to:
   determine that a quantification cycle within a predetermined range is a valid testing.

29. The computer-implemented method of claim 1, further comprising: generate on a machine display a visualization of the dPCR result and a real-time amplification curve formed from corresponding amplification curve values for a selected sample, wherein the visualization aligns the dPCR result and the real-time amplification curve by cycle values of the amplification process.

30. The computer-implemented method of claim 1, wherein the plurality of samples includes thousands of samples producing thousands of reactions.

31. The computer-implemented method of claim 1, wherein a high-density sample support device is employed to support the plurality of samples.

* * * * *